United States Patent [19]

Hartlaub

[11] 4,164,945

[45] Aug. 21, 1979

[54] DIGITAL CARDIAC PACEMAKER MEDICAL DEVICE

[75] Inventor: Jerome T. Hartlaub, New Brighton, Minn.

[73] Assignee: Medtronic, Inc., Minneapolis, Minn.

[21] Appl. No.: 805,726

[22] Filed: Jun. 13, 1977

[51] Int. Cl.² .............................................. A61N 1/36
[52] U.S. Cl. ............................................ 128/419 PG
[58] Field of Search ....................... 128/419 P, 419 PG

[56] References Cited

U.S. PATENT DOCUMENTS

| 3,805,796 | 4/1974 | Terry, Jr. et al. | 128/419 PG |
| 3,842,844 | 10/1974 | Alferness | 128/419 PG |
| 4,049,004 | 9/1977 | Walters | 128/419 PG |

Primary Examiner—William E. Kamm
Attorney, Agent, or Firm—Harry W. Barron; Joseph F. Breimayer

[57] ABSTRACT

A digitally controlled pulse generator includes a low frequency oscillator and a high frequency oscillator and logic means responsive to said oscillators so that the time between stimulating pulses provided by such pulse generator is determined by the low frequency oscillator and the width of the stimulating pulse is determined by the high frequency oscillator. In addition, logic means are included for comparing the frequency of the low frequency oscillator against the high frequency oscillator to insure against pacemaker runaway.

51 Claims, 1 Drawing Figure

Fig.1

DIGITAL CARDIAC PACEMAKER MEDICAL DEVICE

This invention relates to cardiac pacemakers, and more particularly to a digitally controlled pulse generator.

In the prior art, several digitally controlled pulse generators have been described. For examples of these devices reference is made to U.S. Pat. Nos. 3,557,796 in the name of John W. Keller, Jr., et.al., No. 3,833,005 in the name of Robert C. Wingrove, and No. 3,870,050 in the name of Wilson Greatbatch.

Common in each of these disclosures in an oscillator running at a relatively high rate which provides a series of timing pulses to a counter. Logic means are coupled to the counter which decodes the count to determine the time at which a stimulating pulse is to be applied and the duration of such stimulating pulse. In order to have adequate control over the duration of the stimulating pulse, it is necessary that the frequency of the oscillator providing the timing pulses be such that the duration between timing pulses is considerably less than the duration of the stimulating pulse. For instance, if it is desired that the duration of the stimulating pulse by variable between one-half and one millisecond in increments of tenths of a millisecond, it would be necessary that the frequency of the oscillator be at least 10,000 hertz. Even at this frequency, adequate width control may not be obtained.

With an oscillator frequency of 10,000 hertz, it would be required to provide a counter capable of counting to at least 10,000 if the maximum time between stimulating pulses from the pulse generator were one second or, in other words, if the minimum heart rate which is controlled by the pulse generator was sixty beats per minute. Providing this large number of pulses requires extensive use of energy because, each time a pulse is provided, an additional drain on the power source of the pulse generator occurs. In the case of implanted pulse generators, it is desirable to minimize the drain on the power source to extend the life of the pulse generator and thereby subject the patient to less frequent surgical procedures.

Another disadvantage of the prior art disclosures utilizing only a single oscillator is that due to random component failure an oscillator may begin oscillating at a frequency much greater than its designed frequency. If this is the case, a fixed counter causing a stimulating pulse to be provided after a certain number of timing pulses have occurred will provide such pulses at a too rapid rate, which may cause serious problems with the subject utilizing the pacemaker. This is a phenomenon known as pacemaker runaway and, if not controlled, could ultimately lead to ventricular fibrillation and death. With only a single oscillator providing timing signals, there is no direct way by which the frequency of the oscillator can be independently compared to insure that it is operating within prescribed limits.

A feature lacking in prior art digital pulse generators used as a part of a pacemaker system is the inclusion of refractory logic to render the pulse generator nonresponsive to cardiac signals for a fixed time after the provision of the stimulus pulse. Another feature lacking in these prior art pulse generators is reversion logic to cause a ventricular inhibited (demand) pulse generator to revert to asynchronous operation in the presence of large continuous wave interference signals. Both of these features are present in prior art analog devices and are implemented by capacitive timing circuits within the devices. However, as with any analog capacitive timing circuit, reliability problems are associated with capacitors, not to mention their high cost. Further it is difficult to vary the parameters of the refractory or reversion times.

In accordance with a preferred embodiment of this invention, there is provided a digitally controlled medical device capable of providing output pulses of a certain duration at a determined rate. The device comprises a first oscillator for providing a timing signal at a first periodic rate and a second oscillator for providing a second timing signal at a second periodic rate, where the second rate is greater than the first rate. In addition, there is provided control means responsive to the first timing signal for controlling the predetermined rate and responsive to the second timing signal for controlling the certain duration.

A preferred embodiment in a cardiac pulse generator of this invention is hereinafter described with specific reference being made to the following FIGURE, in which.

Figure 1:
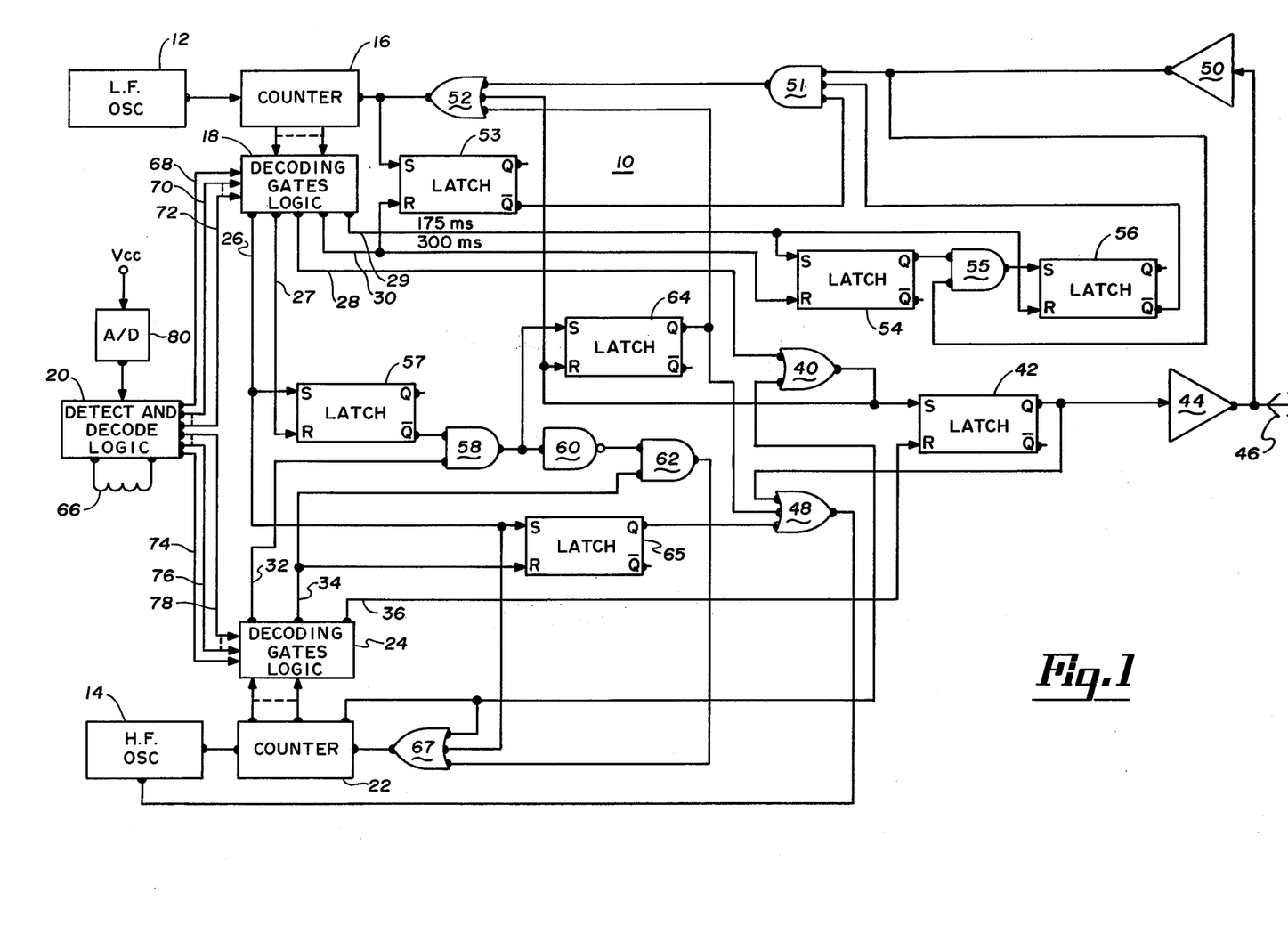
FIG. 1 shows a block diagram of a digitally controlled pulse generator used in conjunction with a lead connected between the pulse generator and a person's heart to form a pacemaker.

Referring now to the FIGURE, digitally controlled pulse generator 10 includes low frequency oscillator 12, and high frequency oscillator 14. Low frequency oscillator 12 may be selected to oscillate at a rate of 200 hertz, and high frequency oscillator 14 may be selected to oscillate at a rate of 20 kilohertz when an enable signal is applied to the enable (E) input thereof.

The output of oscillator 12 is applied to a counter 16 which may include eight stages. Counter 16 is designed to increment the count it contains by one each time a pulse from the low frequency oscillator 12 is applied to the clock (C) input thereof. In addition, whenever a pulse is applied to the reset (R) input of counter 16, the count therein is then changed to a count of zero, that is, each of the eight stages become reset.

The outputs from each of the eight stages of counter 16 are provided to a series of decoding gates which, in a known manner, provide digital signals upon counter 16 reaching selected counts. In a manner which will be described in more detail hereafter, decoding gates 18 may include a series of gates which are enabled by selected signals applied thereto from detecting and decoding logic 20.

High frequency oscillator 14 is designed to be selectively enabled by the application of a signal to the enable (E) input thereof. When enabled, oscillator 14 provides a pulse signal having a frequency of 20 kilohertz to counter 22. Counter 22 may be a sixteen stage counter which will be described in more detail hereafter. The outputs from the first seven stages of counter 22 are coupled to the gates in decoding gates logic 24. Decoding gates logic 24 may be a series of enabled AND gates coupled to the various outputs of counter 22 in such a manner that specific counts in counter 22 can be manifested by signals at the output of decoding gates logic 24.

Decoding gates logic 18 provides five output pulse signals at outputs 26, 27, 28, 29 and 30. A signal appears at output 26 whenever the count in counter 16 is one and a signal appears at output 27 wherever the count in counter 16 is two. A signal appears at output 28 after the time required for counter 16 to count from zero to a count equivalent to the time between stimulating pulses provided by pulse generator 10. For instance, if it were desired to provide pulses at a rate of one per second, then a gate within decoding gates logic 18 would be responsive to counter 16 attaining a count of 200 and at that time provide an output signal to output 28. This gate could be an AND gate having the third, seventh, and eighth stage outputs coupled thereto. Outputs 29 and 30 are used to control the refractory and reversion periods of pulse generator 10. Output 29 may be connected to provide a signal 175 milliseconds after counter 16 has been reset, or in other words, when counter 16 reaches a count of thirty-five, and output 30 may be connected to provide a signal 300 milliseconds after counter 16 has been reset, or, in other words, when counter 16 reaches a count of sixty. As will be explained in more detail hereinafter, the counts at which the gates of logic 18 respond can be selectively altered by the operation of detecting and decoding logic 20.

Decoding gates logic 24 has three outputs 32, 34, and 36 at each of which appears a pulse signal at designated counts of counter 22. The gates within logic 24 are arranged so that a signal appears at output 36 at a time after counter 22 is reset equal to one half the time between pulses of low frequency oscillator 12, or when counter 22 reaches a count of fifty. In the case of output 34, a signal appears one count of counter 22 after the signal appears at output 32. A signal appears at output 36 at a time after counter 22 is reset equal to the time of the stimulating pulse. If for instance the stimulating pulse has a duration of one msec, the gates providing the output pulse to output 36 would detect a count of twenty in counter 22.

In order to control the stimulating pulse, two times are important. The first time is the time between stimulating pulses and the second time is the duration of the stimulating pulse. Because the time between stimulating pulses is relatively long, low frequency oscillator 12 and counter 16 are used for control and because the duration of the stimulating pulse is relatively small, high frequency oscillator 14 and counter 22 are used for control. In addition OR gate 40, latch 42 and output amplifier 44 are used to provide the stimulating pulse.

Output 28 from logic 18 is coupled through one input of OR gate 40 to the set input of latch 42. As is well known in the art, a latch circuit, such as latch 42, is a bistable device having a Q and a $\overline{Q}$ output and a set (S) and reset (R) input. When a pulse signal is applied to the set input, a logic "1", or positive, voltage is provided from the Q output and a logic "0", or ground, voltage is provided from the $\overline{Q}$ output. These voltages remain until a logic "1" signal is applied to the reset input, which signal causes a logic "0" to be provided from the Q output and a logic "1" to be provided from the $\overline{Q}$ output. Again, this condition of the latch remains until a logic "1" signal is provided to the set input. A latch circuit can be composed of a pair of two input AND gates having the outputs cross coupled to an input with the other gate input being the set or reset inputs of the latch.

The Q output from latch 42 is provided to the input of output amplifier 44, the output of which is coupled to the lead 46. Amplifier 44 is designed so that whenever the signal applied thereto from the Q output from latch 42 is logic "1", a stimulating pulse is applied from amplifier 44 to lead 46. The Q output from latch 42 is also provided through OR gate 50 to reset counter 16 to a zero count.

Output 36 from logic 24 is coupled to the reset input of latch 42. Whenever a pulse is provided to reset latch 42, the logic "1" voltage at the Q output of latch 42 becomes logic "0" and the stimulating pulse provided from the output of amplifier 44 to lead 46 ceases. Thus, the stimulating pulse from amplifier 44 is only provided between the time a signal is provided to set latch 42 and a signal is provided to reset latch 42, or, in other words, between the time a signal appears at output 28 of logic 18 and output 36 of logic 24.

The Q output from latch 42 is also applied to one input of an OR gate 48, the output of which is coupled to the enabled input of high frequency oscillator 14 as an enable signal to cause oscillator to begin applying pulses to counter 22. Thus, at the same time a signal appears at output 28 of logic 18 and sets latch 42, oscillator 14 becomes enabled and begins providing pulses to counter 22. After a count is reached in counter 22 manifesting the desired pulse width, a signal appears at output 36 and resets latch 42, thereby terminating the stimulus pulse at the desired time, and at the same time causing oscillator 14 to cease providing pulses to counter 22.

Pulse generator 10 is designed to operate as a ventricular inhibited, or demand, type of pacemaker, that is, the heart is given an opportunity to provide a beat naturally prior to a certain time and only in the event that the heart does not naturally beat within that time, is a stimulating pulse provided from amplifier 44 to lead 46. As is well known in the art, lead 46 is utilized as both a transmitting and receiving lead, that is, it transmits the stimulating pulse from amplifier 44 to the heart and also transmits electrical signals from the heart to pulse generator 10.

Connected to lead 46 is sensing amplifier 50 which senses the electrical signals from the heart occurring as a result of a heartbeat and provides a compatible digital signal at its output manifesting the occurrence of such beat. Amplifier 50 may be designed to detect the R wave and not P or T waves, of the electrocardiac wave form by the inclusion therein of appropriate frequency filters and threshold devices. The output from amplifier 50 is provided through one input of normally enabled three input AND gate 51 to one input of OR gate 52, the output of which is coupled to the reset input of counter 16 to reset counter 16 to a count of zero. Thus, if a natural heartbeat occurs prior to the time the count in counter 16 reaches the value sufficient to cause a signal to appear at output 28, the count in counter 16 will be reset to zero, thereby initiating a new cycle for pulse generator 10 and preventing the provision of a signal at output 28 to initiate a stimulating pulse.

As is well known in the art, it is desirous to render a ventricular inhibited pacemaker as refractory for a certain period of time (e.g. 300 milliseconds) after the provision of a stimulating pulse, if provided, or if not provided, after the occurrence of a natural heartbeat. It should be noted that during the refractory time pulse generator 10 does not respond to any signals applied thereto over lead 46. The refractory function is controlled by latch 53 in conjunction with AND gate 51 and OR gate 52.

The set (S) input of latch 53 is connected to the output of OR gate 52 and the reset (R) input of latch 53 is coupled to output 30 from logic 18, that is the 300 millisecond timing signal. The $\overline{Q}$ input of latch 53 is coupled to a second input of AND gate 51 and acts to disable AND gate 51 wherever latch 53 is set, that is whenever the $\overline{Q}$ output thereof is logic "0". In operation, at the earlier of the time a signal is sensed by amplifier 50 thereby causing a pulse signal to be provided at the output of OR gate 52 or a stimulating pulse is initiated by a pulse signal appearing at the output of OR gate 40, which pulse is applied through OR gate 52, latch 53 becomes set by the signal at the output of OR gate 52, rendering the $\overline{Q}$ output logic "0" and disabling AND gate 51 from passing further signals from sensing amplifier 50. At the same time, counter 61 is reset to zero and begins counting again. When the count in counter 16 reaches the number sixty, corresponding to the passage of 300 milliseconds at a frequency of 200 hertz, latch 53 is reset, thereby causing the $\overline{Q}$ output to return to logic "1" and again enabling AND gate 51 to pass signals from amplifier 50.

Also, as is well known in the art, it is desirous that a ventricular inhibited pacemaker revert to an asynchronous mode of operation in the presence of a continuous interference signal strong enough to be detected by amplifier and reset counter 16 the most common of which interference signal is a sixty hertz signal. This reversion circuit of pulse generator 10 includes latch 54, AND gate 55 and latch 56, in conjunction with AND gate 51 and the timing signals at outputs 29 and 30 of logic 18. Specifically, the 175 millisecond timing signal at output 29 is coupled to the set (S) input of latch 54 and the reset (R) input of latch 56 and the 300 millisecond timing signal at output 30 is coupled to the reset (R) input of latch 54. The Q output from latch 54 is coupled to one input of AND gate 55 and the other input of AND gate 55 is coupled to the output of sensing amplifier 50. The output of AND gate 55 is coupled to the set (S) input of latch 56 and the $\overline{Q}$ output of latch 56 is coupled as the third input to AND gate 51.

In operation, the reversion circuit looks for a response by the sensing amplifier during the time window of 125 millisecond duration at the end of the refractory period. It should be noted that the sensing amplifier is designed to filter certain low frequency and low magnitude signals so that, in particular, T waves do not cause a pulse to be provided at the output thereof. With the selection of a 125 millisecond time window, any signal having a high enough magnitude and a rate of eight hertz or more will cause at least one pulse to occur during the time window.

In the reversion circuit of pulse generator 10, latch 54 is set by the signal at output 29 of logic 18 and latch 56 is reset 175 milliseconds after counter 16 is reset and remains set for 125 milliseconds, that is, until counter 16 causes a signal to appear at output 30 of logic 18. During the 125 millisecond time latch 54 is set prior to being reset, the Q output is logic "1" and enables AND gate 55 to pass any pulse signal provided by sensing amplifier 50. Should such a pulse signal occur it is coupled through AND gate 55 and sets latch 56 thereby causing the $\overline{Q}$ output to become logic "0" and disabling AND gate 51. With AND gate 51 disabled, the ventricular inhibited mode of pulse generator 10 is disabled, since no sensed heart-beats can pass through AND gate 51, and pulse generator 10 operates in the asynchronous mode AND gate 51 is reset at 175 milliseconds of the next cycle by the signal at output 29 of logic 18 and if the interfering signal has disappeared, latch 56 will not be again set; otherwise latch 56 will be set and asynchronous operations will continue.

One advantage of having the two oscillators 12 and 14 in pulse generator 10 is that a comparison between the two can be made to pevent pacemaker runaway. To accomplish this, a comparison circuit consisting of latches 57, 64 and 65, AND gates 58 and 62 and inverter 60 are provided and coupled as follows.

Output 26 from logic 18 is coupled to the set input of latch 57 and output 28 from logic 18 is coupled to the reset input of latch 57. The $\overline{Q}$ output of latch 57 and output 32 from logic 24 are coupled as the two inputs to AND gate 58, the output of which is applied through inverter 60 to one input of AND gate 62. Output 34 from logic 24 is coupled to the other input of AND gate 62. The output of AND gate 62 is coupled to one input of OR gate 67, the output of which is coupled to the reset input of counter 22 to reset counter 22 to a count of zero. The output from AND gate 58 is also coupled to the set input of latch 64, and the output from OR gate 40 is coupled to the reset input of latch 64. Output 26 from logic 18 is coupled to the set input of latch 67 and output 34 from logic 24 is coupled to the reset input of latch 67. The Q output of latch 67 is coupled to a second input of OR gate 48 and the Q output from latch 64 is coupled to a third input of OR gate 48.

In the operation of the comparison circuit of pulse generator 10, the signal at output 26 of logic 18 is utilized to set latches of 57 and 65 shortly after counter 16 is reset, that is, one count thereafter. The logic "1" signal at the Q output of set latch 65 is applied through OR gate 48 to enable oscillator 14 to provide pulses to counter 22. The logic "0" $\overline{Q}$ signal at the output of set latch 57 is applied to disable AND gate 58 from passing any signal applied to the other input thereof.

One count of oscillator 12 later, the output signal at output 27 of logic 18 resets latch 57 thereby causing the $\overline{Q}$ output to return to logic "1" and reenable AND gate 58 to pass signals applied to the other input thereof. Under normal operation, a signal will appear at output 32 of logic 24 at approximately the middle of the time window during which AND gate 58 is disabled and thus will not be passed through AND gate 58 to set latch 64. One pulse of oscillator 14 after a signal appears at output 32, a signal will appear at output 34 and reset latch 65, thereby removing the enabled signal applied through OR gate 48 to oscillator 14.

The only time that a signal from output 32 occurs while AND gate 58 is not disabled, and thus be passed through AND gate 58, is when the frequency of oscillator 12 more than doubles from, for instance, 200 hertz to 400 hertz or greater, or if the frequency of oscillator 14 drops in half or more, from, for example, from 20 kilohertz to 10 kilohertz. In the latter case, there is no danger of a pacemaker runaway; however, in the former case, if the frequency of oscillator 12 becomes too high the heart will be paced at too rapid a rate and serious consequences could result from this situation. To prevent the heart from being paced at too rapid a rate, the logic "1" pulse signal at the output of AND gate 58 sets latch 64, thereby causing the Q output thereof to become logic "1". This logic "1" signal is applied through OR gate 52 to maintain counter 16 in a continual reset condition. In addition, the logic "1" signal from the Q output of latch 64 is applied through OR gate 48 to enable high frequency oscillator 14. This condition will remain until latch 64 is reset at the time the pulse generator 10 stimulating pulse is provided, that is, at the time a signal appears at the output of OR gate 40.

With oscillator 14 enabled, counter 22 counts up through the full sixteen stages thereof. At the time stage sixteen becomes set, some 1.64 seconds after counter 22 had a zero count therein, a signal is applied from the sixteenth stage through OR gate 40 to set latch 42, thereby causing a stimulating pulse to commence being applied to lead 46. The pulse at the output of OR gate 40 is also applied to reset latch 64, thereby removing the reset signal from counter 16, and one of the oscillator 14 enable signals applied through OR gate 48. At the time, the output signal from stage sixteen is applied through OR gate 67 to reset counter 22 to a zero count and the signal causing the stimulating pulse at the Q output of latch 42 is applied through OR gate 48 to enable oscillator 14. This causes oscillator 14 to count upward from zero until a signal appears at output 36 to reset latch 42 and remove the enabling signal at the proper time.

With counter 16 no longer maintained continually reset, a signal will appear at output 26 shortly after the termination of the stimulating pulse. This causes a new comparison to be made between the frequencies of oscillator 12 and oscillator 14, and if the frequency of oscillator 12 is too high or the frequency of oscillator 14 is too low, a pulse appears at the output of AND gate 58 and counter 22 will again count the pulses from oscillator 14 until such time as the sixteenth stage again becomes set. In other words, in this mode of operation, pulse generator 10 is operating in an asynchronous mode of providing stimulating pulses.

In the event oscillator 12 is operating properly and a signal appears at output 32 prior to the time latch 57 becomes set, a logic "1" output signal is provided from AND gate 62 through OR gate 67 to reset counter 22 to a count of zero. If desired, the output from amplifier 50 could be gated through OR gate 67 to the reset input of counter 22 during this mode of operation to change the device to a ventricular inhibited, or demand, pacemaker and appropriate signals from counter 24 could be gated to latches 53, 54 and 56 to include the refractory and reversion functions.

Pulse generator 10 is provided with a capacity to vary both the rate and pulse duration and the refractory or reversion times of pulse generator 10. This is accomplished by detecting and decoding logic 20 which receives radio frequency coded information radiated to antenna 66 in a known manner, such as is described in the abovementioned U.S. Pat. No. 3,833,005. Upon decoding this information, selected signals are applied over lines 68, 70 . . . and 72, which are applied from logic 20 to logic 18. Each of these lines 68, 70 . . . and 72 are coupled to a different set of gates relative to the outputs 28, 29 and 30 from logic 18 so that the count of counter 16 necessary to cause signals to appear at outputs 28, 29 and 30 can be varied, thereby varying the rate at which the stimulus pulse is provided and the refractory and reversion times. In addition, logic 20 provides signals over lines 74, 76, . . . and 78, which, in turn, are applied to logic 24 for varying the count necessary to cause a signal to appear at output 36, thereby varying the pulse duration. In addition, signals may inhibit the operation of AND gate 58 to disable the comparison function in the event the problem causing AND gate 58 to provide a pulse is that the frequency of oscillator 14 is too slow.

Logic 20, in addition to being responsive to the radio frequency signals radiated to antenna 66, also is responsible to a signal from analog-to-digital (AD) convertor 80 which provides a digital word manifesting the magnitude of the power source voltage. This digital word can be processed by logic 22 to automatically vary the pulse width in accordance with the power source voltage. Thus, as the voltage in the power source begins to decrease as a result of age, it is necessary to increase the stimulating pulse width. Circuitry within logic 20 can cause appropriate signals to be provided over lines 74, 76, . . . and 78 in accordance with the value of digital signal applied thereto from the analog-to-digital convertor 80.

What is claimed is:

1. A digitally controlled medical device capable of providing output pulses of a certain duration at a determined rate, said device comprising:
   a first oscillator for providing a first timing signal at a first periodic rate;
   a second oscillator for providing a second timing signal at a second periodic rate; and
   control means responsive to said first timing signal for controlling said predetermined rate and for enabling said second oscillator to provide said second timing signal and responsive to said second timing signal for controlling said certain duration and for disabling said second oscillator from providing said second timing signal at times other than said certain time.

2. The invention according to claim 1:
   wherein each of said first and second timing signals are pulse signals;
   wherein the time between timing pulses of said first timing signal is greater than said certain duration and said first periodic rate is a whole number multiple of said determined rate; and
   wherein said certain duration is a whole number multiple of the time between timing pulses of said second timing signal.

3. The invention according to claim 1 wherein said control means includes:
   a first counter responsive to said first timing signal for incrementing its count upon the occurrence of each pulse of said first timing signal;
   a second counter responsive to said second timing signal for incrementing its count upon the occurrence of each pulse of said second timing signal;
   means responsive to said first counter achieving a first count for enabling said second oscillator to provide said second timing signal to said second counter and for causing the commencement of the provision of said device output pulse, said means further being responsive to said second counter achieving a second count for terminating the provision of said device output pulse; and
   means for resetting the counts of said first and second counter and disabling said second oscillator from providing said second timing signal to said second counter.

4. The invention according to claim 3 wherein the means for resetting includes a sensing amplifier for sensing a response and for resetting said first counter upon the occurrence of said sensed response.

5. The invention according to claim 4 wherein said control means includes refractory means for preventing, for a given period after said first counter is reset, any further resetting of said first counter as a result of said sensing amplifier sensing a response.

6. The invention according to claim 4 wherein said control means includes reversion means for sensing the presence of a large interference signal sensed by said sensing amplifier and for preventing any resetting of said first counter whenever said interference signal is sensed.

7. The invention according to claim 6 wherein said reversion means includes means responsive to said first counter achieving selected counts defining a time window related to the low frequency of said interference signal and means for determining whether said sensing amplifier senses any signal during said defined time window.

8. The invention according to claim 7 wherein said defined time window occurs within a short time after said sense amplifier senses a response.

9. The invention according to claim 7 wherein said control means includes refractory means for preventing, for a given period after said first counter is reset, any further resetting of said first counter as a result of said sensing amplifier sensing a response.

10. The invention according to claim 1 wherein said control means further includes means for selecting one of a plurality of determined rates and one of a plurality of certain durations in response to externally applied control signals.

11. The invention according to claim 1 wherein said control means further includes means for selecting one of a plurality of determined rates and one of a plurality of certain durations in response to internal parameters of said device.

12. The invention according to claim 11 wherein said control means further includes means for selecting one of a plurality of determined rates and one of a plurality of certain durations in response to externally applied control signals.

13. The invention according to claim 1 wherein said second rate is greater than said first rate.

14. A digitally controlled medical device capable of providing output pulses of a certain duration of a determined rate, said device comprising:
 a first oscillator for providing a first timing signal at a first periodic rate;
 a second oscillator for providing a second timing signal at a second periodic rate; and
 control means responsive to said first timing signal for controlling said predetermined rate and responsive to said second timing signal for controlling said certain duration;
 wherein said device further includes means for comparing said first and second timing signals and for inhibiting said control means response to said first timing signal in the event said first periodic rate exceeds a certain limit relative to said second periodic rate.

15. A digitally controlled medical device capable of providing output pulses of a certain duration at a determined rate, said device comprising:
 a first oscillator for providing a first timing signal at a first periodic rate;
 a second oscillator for providing a second timing signal at a second periodic rate; and
 control means responsive to said first timing signal for controlling said predetermined rate and responsive to said second timing signal for controlling said certain duration;
 wherein said control means includes:
 a first counter responsive to said first timing signal for incrementing its count upon the occurrence of each pulse of said first timing signal;
 a second counter responsive to said second timing signal for incrementing its count upon the occurrence of each pulse of said second timing signal;
 means responsive to said first counter achieving a first count for enabling said second timing signal to be provided to said second counter and for causing the commencement of the provision of said device output pulse, said means further being responsive to said second counter achieving a second count for terminating the provision of said device output pulse; and
 means for resetting the counts of said first and second counter and disabling said second timing signal from being applied to said counter;
 wherein the means for resetting includes a sensing amplifier for sensing a response and for resetting said first counter upon the occurrence of said sensed response;
 wherein said control means includes refractory means for preventing, for a given period after said first counter is reset, any further resetting of said first counter as a result of said sensing amplifier sensing a response; and
 wherein said refractory means includes latch means which is set by either the provision of a device output pulse or the sensing of a response by said sensing amplifier and which is reset by said first counter achieving a count equivalent to said given period.

16. A digitally controlled medical device capable of providing output pulses of a certain duration at a determined rate, said device comprising:
 a first oscillator for providing a first timing signal at a first periodic rate;
 a second oscillator for providing a second timing signal at a second periodic rate; and
 control means responsive to said first timing signal for controlling said predetermined rate and responsive to said second timing signal for controlling said certain duration;
 wherein said control means includes:
 a first counter responsive to said first timing signal for incrementing its count upon the occurrence of each pulse of said first timing signal;
 a second counter responsive to said second timing signal for incrementing its count upon the occurrence of each pulse of said second timing signal;
 means responsive to said first counter achieving a first count for enabling said second timing signal to be provided to said second counter and for causing the commencement of the provision of said device output pulse, said means further being responsive to said second counter achieving a second count for terminating the provision of said device output pulse; and
 means for resetting the counts of said first and second counter and disabling said second timing signal from being applied to said counter;
 wherein the means for resetting includes a sensing amplifier for sensing a response and for resetting said first counter upon the occurrence of said sensed response;
 wherein said control means includes reversion means for sensing the presence of a large interference signal sensed by said sensing amplifier and for preventing any resetting of said first counter whenever said interference signal is sensed;

wherein said reversion means includes means responsive to said first counter achieving selected counts defining a time window related to the low frequency of said inteference signal and means for determining whether said sensing amplifier senses any signal during said defined time window;

wherein said control means includes refractory means for preventing, for a given period after said first counter is reset, any further resetting of said first counter as a result of said sensing amplifier sensing a response; and wherein said refractory means includes latch means which is set by either the provision of a device output pulse or the sensing of a response by said sensing amplifier and which is reset by said first counter achieving a count equivalent to said given period.

17. The invention according to claim 16 wherein said defined time window occurs during said given period.

18. A digitally controlled medical device capable of providing output pulses of a certain duration at a determined rate, said device comprising:

a first oscillator for providing a first timing signal at a first periodic rate;

a second oscillator for providing a second timing signal at a second periodic rate; and control means responsive to said first timing signal for controlling said predetermined rate and responsive to said second timing signal for controlling said certain duration;

wherein said control means includes:

a first counter responsive to said first timing signal for incrementing its count upon the occurrence of each pulse of said first timing signal;

a second counter responsive to said second timing signal for incrementing its count upon the occurence of each pulse of said second timing signal;

means responsive to said first counter achieving a first count for enabling said second timing signal to be provided to said second counter and for causing the commencement of the provision of said device output pulse, said means further being responsive to said second counter achieving a second count for terminating the provision of said device output pulse; and means for resetting the counts of said first and second counter and disabling said second timing signal from being applied to said counter;

wherein the means for resetting includes a sensing amplifier for sensing a response and for resetting said first counter upon the occurrence of said sensed response; and wherein said means for resetting further includes means, responsive to said second counter achieving a third count prior to the time said first counter achieves a fourth count, for resetting said second counter, said third counts occurring prior to the time fourth count occurs so long as said first oscillator provides said first timing signal at said first periodic rate and said second oscillator provides said second timing signal at said second periodic rate.

19. A digitally controlled medical device capable of providing output pulses of a certain duration at a determined rate, said device comprising:

a first oscillator for providing a first timing signal at a first periodic rate;

a second oscillator for providing a second timing signal at a second periodic rate; and control means responsive to said first timing signal for controlling said predetermined rate and responsive to said second timing signal for controlling said certain duration;

wherein said control means includes:

a first counter responsive to said first timing signal for incrementing its count upon the occurrence of each pulse of said first timing signal;

a second counter responsive to said second timing signal for incrementing its count upon the occurrence of each pulse of said second timing signal;

means responsive to said first counter achieving a first count for enabling said second timing signal to be provided to said second counter and for causing the commencement of the provision of said device output pulse, said means further being responsive to said second counter achieving a second count for terminating the provision of said device output pulse; and means for resetting the counts of said first and second counter and disabling said second timing signal from being applied to said counter;

wherein said control means further includes:

means responsive to said first counter for providing, prior to said counter achieving said first count, third and fourth signals manifesting a time window related to the frequency of said first oscillator;

means responsive to said second counter for providing a fifth signal during said time window so long as said first and second oscillators provide signals at said respective first and second periodic rates; and means responsive to said third, fourth and fifth signals for providing a sixth signal whenever said fifth signal does not occur in time relation between said third and fourth signals.

20. The invention according to claim 19 wherein said control means further includes means responsive to said sixth signal for preventing said first counter from achieving said first count and for enabling said second timing signal to be provided to said second counter; and means responsive to said second counter achieving a third count to cause the commencement of the provision of said device output pulse, and for resetting said second counter to allow said second counter to achieve said second count.

21. The invention according to claim 20:

wherein said means responsive to said second counter provides a sixth signal after providing said fifth signal;

wherein said third and fourth signals are provided after said first counter is reset;

wherein said third signal is applied to reset said second counter; and wherein said control means further includes:

means responsive to said third and sixth signals for enabling said second timing signal to be provided between the times said third and sixth signals are provided;

means for determining whether said fifth signal is provided prior to the time said fourth signal is provided; and means for inhibiting said first counter from providing said first signal and for enabling said second oscillator to allow said second counter to provide a seventh signal to cause the commencement of the provision of said device output pulse.

22. A digitally controlled cardiac pulse generator capable of providing to a lead affixed to a subject's heart, a stimulating pulse, said pulse occurring at a fixed rate and having a sufficient magnitude and duration to cause a contraction of said heart, said pulse generator comprising:
a first oscillator for continuously providing a first periodic signal in which the pulses occur at a first rate greater than said fixed rate;
a second oscillator for providing, when enabled, a second periodic pulse signal at a second rate greater than said first rate in which the time period between pulses is less than said stimulating pulse duration;
a first resettable counter responsive to said first pulse signal for counting the pulse applied thereto;
a second resettable counter responsive to said second pulse signal for counting the pulses applied thereto;
a bistable circuit which, when set, causes said stimulating pulse to be provided;
means responsive to the occurrence of said first counter means reaching a first count related to said fixed rate for setting said bistable circuit and for enabling said second oscillator to provide said second pulse signal;
means responsive to the occurrence of said second counter means reaching a second count related to the duration of said stimulating pulse for resetting said bistable circuit; and
means for resetting said first and second counters and disabling said second oscillator.

23. The invention according to claim 22 wherein said means for resetting includes means responsive to the provision of said stimulating pulse to reset said first counter; and sensing means for sensing the occurrence of contractions of said subject's heart for resetting said first counter in response to said sensed contraction.

24. The invention according to claim 23:
wherein said pulse generator further includes means for providing signals in response to the occurrence of said first counter reaching third and fourth counts defining a time window and means responsive to said second counter reaching a fifth count;
wherein said means for resetting further includes:
means for enabling said second oscillator in response to the signal provided in response to said first counter reaching said third count; and
means for providing a signal to reset said second counter and disable said second oscillator; and
means in response to said second counter reaching said fifth count prior to said first counter reaching said fourth count;
wherein the time necessary for said second counter to reach said fifth count is less than the time required for said first counter to reach said fourth count so long as said first and second oscillators provide signals at said first and second rates respectively.

25. The invention according to claim 24:
wherein said pulse generator further includes means for providing a signal in response to said second counter reaching a sixth count;
wherein said means for resetting further includes:
means for maintaining said second oscillator enabled until a stimulating pulse is provided whenever said first counter reaches said fourth count prior to said second counter reaching said fifth count; and
means for resetting said second counter upon said second counter reaching said sixth count; and
wherein said pulse generator further includes means responsive to said second counter reaching said sixth count for setting said bistable circuit.

26. The invention according to claim 25 wherein said pulse generator further comprises means for selectively altering said fixed rate and sufficient duration in response to external signals applied thereto.

27. The invention according to claim 26 wherein said means for selectively altering includes means for detecting and decoding said external signals and means for selectively changing said first and second counts in response to the code of said detected and decoded external signals.

28. The invention according to claim 26 wherein said pulse generator means further includes means for altering said sufficient duration in response to internal parameters of said pulse generator.

29. The invention according to claim 23 wherein said pulse generator further includes refractory means for inhibiting said sensing means from again resetting said first counter for a fixed time after said first counter is reset.

30. The invention according to claim 29:
wherein said fixed time is determined by said first counter reaching a certain count; and
wherein said refractory means includes means for providing a signal in response to said first counter reaching said certain count and latch means set by the resetting of said first counter and reset by said signal provided when said first counter reaches said certain count.

31. The invention according to claim 29 wherein said pulse generator further includes reversion means for sensing the presence of an interference signal sufficiently large to be sensed by said sensing amplifier and for preventing any resetting of said first counter whenever said interference signal is sensed.

32. The invention according to claim 31 wherein said reversion means includes means responsive to said first counter reaching a pair of counts defining a reversion time window related to the low frequency limit of said interference signal and means for determining whether said sensing amplifier senses any signal during said defined time window.

33. The invention according to claim 32 wherein the later one of said counts defining said reversion time window is coincident with said certain count.

34. The invention according to claim 33 wherein said reversion means includes means for providing first and second reversion signals in response to said first counter achieving respective first and second reversion counts, a first latch, a second latch, first gating means and second gating means, said first gating means being responsive to the application thereto of any signal sensed by said sensing means for providing a signal, when enabled, upon the occurrence of said sensed signal, said second gating means passing said sensing means signal to reset said first counter except when disabled, said first latch being responsive to said first and second reversion signals to be in a state during the interim therebetween to enable said first gating means, said first gating means signal being applied to set said second latch and the later occurring one of said first and second reversion signals being applied to reset said second latch, said second latch, being coupled to disable said second gating means when said latch is set.

35. The invention according to claim 23 wherein said reversion means includes means responsive to said first counter reaching a pair of counts defining a reversion time window related to the low frequency limit of said interference signal and means for determining whether said sensing amplifier senses any signal during said defined time window.

36. The invention according to claim 35 wherein the later one of said counts defining said reversion time window is coincident with said certain count.

37. The invention according to claim 36 wherein said reversion means includes means for providing first and second reversion signals in response to said first counter achieving respective first and second reversion counts, a first latch, a second latch, first gating means and second gating means, said first gating means being responsive to the application thereto of any signal sensed by said sensing means for providing a signal, when enabled, upon the occurrence of said sensed signal, said second gating means passing said sensing means signal to reset said first counter except when disabled, said first latch being responsive to said first and second reversion signals to be in a state during the interim therebetween to enable said first gating means, said first gating means signal being applied to set said second latch and the later occurring one of said first and second reversion signals being applied to reset said second latch, said second latch, being coupled to disable said second gating means when said second latch is set.

38. A digitally controlled medical device capable of providing output pulses of a certain duration at a predetermined rate, said device comprising:
a first oscillator for providing a pulse chain signal at a first rate;
a second oscillator for providing, when enabled, a pulse chain signal at a second rate;
counter means responsive to said first and second oscillator signals for incrementing its count upon the occurrence of each pulse of said first and second oscillator signals;
control means responsive to said counter means achieving a first count in response to said first oscillator signal for enabling said second oscillator to provide said second oscillator signal to said counter means and for causing the commencement of the provision of said device output pulse, said control means further being responsive to said counter means achieving a second count in response to said second oscillator signal to terminate the provision of said device output pulse; and
means for resetting the counts of said counter and disabling said second oscillator from providing said second oscillator signal to said counter.

39. The invention according to claim 38 wherein the means for resetting includes a sensing amplifier for sensing a response and for resetting said counter upon the occurrence of said sensed response.

40. The invention according to claim 39 wherein said control means includes refractory means for preventing, for a given period of time after said counter is reset, any further resetting of said counter as a result of said sensing amplifier sensing a response.

41. The invention according to claim 38 wherein said control means includes reversion means for sensing the presence of a large interference signal sensed by said sensing amplifier and preventing any resetting of said counter whenever said interference signal is sensed.

42. The invention according to claim 41 wherein said reversion means includes means responsive to said counter achieving selected counts defining a time window related to the low frequency of said interference signal means for determining whether said sensing amplifier means senses any signals during said defined time window.

43. The invention according to claim 42 wherein said defined time window occurs within a short time after said sense amplifier senses a response.

44. The invention according to claim 41 wherein said control means includes refractory means for preventing for a given period after said counter is reset any further resetting of said counter as a result of said sensing amplifier sensing a response.

45. The invention according to claim 38 wherein said second rate is greater than said first rate.

46. The invention according to claim 38 wherein said control means further includes means for selecting one of a plurality of determined rates and one of a plurality of certain durations in response to externally applied control signals.

47. The invention according to claim 38 wherein said control means further includes means for selecting one of a plurality of determined rates and one of a plurality of certain durations in response to internal parameters of said device.

48. The invention according to claim 47 wherein said control means further includes means for selecting one of a plurality of determined rates and one of a plurality of certain durations in response to externally applied control signals.

49. A digitally controlled medical device capable of providing output pulses of a certain duration at a predetermined rate, said device comprising:
a first oscillator for providing a pulse chain signal at a first rate;
a second oscillator for providing, when enabled, a pulse chain signal at a second rate;
counter means responsive to said first and second oscillator signals for incrementing its count upon the occurrence of each pulse of said first and second oscillator signals;
control means responsive to said counter means achieving a first count in response to said first oscillator signal for enabling said second oscillator to provide said second oscillator signal to said counter means and for causing the commencement of the provision of said device output pulse, said control means further being responsive to said counter means achieving a second count in response to said second oscillator signal to terminate the provision of said device output pulse; and
means for resetting the counts of said counter and disabling said second oscillator signal from being provided to said counter;
wherein the means for resetting includes a sensing amplifier for sensing a response and for resetting said counter upon the occurrence of said sensed response;
wherein said control means includes refractory means for preventing, for a given period of time after said counter is reset, any further resetting of said counter as a result of said sensing amplifier sensing a response; and
wherein said refractory means includes latch means which is set by either the provision of a device output pulse or the sensing of a response by said sensing amplifier and which is reset by said counter achieving a count in response to said first timing signal equivalent to said given period.

50. A digitally controlled medical device capable of providing output pulses of a certain duration at a predetermined rate, said device comprising:

a first oscillator for providing a pulse chain signal at a first rate;

a second oscillator for providing, when enabled, a pulse chain signal at a second rate;

counter means responsive to said first and second oscillator signals for incrementing its count upon the occurrence of each pulse of said first and second oscillator signals;

control means responsive to said counter means achieving a first count in response to said first oscillator signal for enabling said second oscillator to provide said second oscillator signal to said counter means and for causing the commencement of the provision of said device output pulse, said control means further being responsive to said counter means achieving a second count in response to said second oscillator signal to terminate the provision of said device output pulse; and means for resetting the counts of said counter and disabling said second oscillator signal from being provided to said counter;

wherein said control means includes reversion means for sensing the presence of a large interference signal sensed by said sensing amplifier and preventing any resetting of said counter whenever said interference signal is sensed;

wherein said control means includes refractory means for preventing for a given period after said counter is reset any further resetting of said counter as a result of said sensing amplifier sensing a response; and wherein said refractory means includes latch means which is set by either the provision of a device output pulse or the sensing of a response by said sensing amplifier and which is reset by said counter achieving a count in response to said first timing signal equivalent to said given period.

51. The invention according to claim 50 wherein said defined time window occurs during said given period.

* * * * *